United States Patent
Kolos

(10) Patent No.: US 6,932,966 B1
(45) Date of Patent: Aug. 23, 2005

(54) TOPICALLY APPLIED RECONSTITUTED OCEAN WATER MIXTURE AND METHOD OF PRODUCING AND USING THE MIXTURE

(76) Inventor: Edward Kolos, 1301 W. Newport Center Dr., Deerfield Beach, FL (US) 33442

( * ) Notice: Subject to any disclaimer, the term of this patent is extended or adjusted under 35 U.S.C. 154(b) by 45 days.

(21) Appl. No.: 10/465,674

(22) Filed: Jun. 20, 2003

Related U.S. Application Data

(63) Continuation-in-part of application No. 09/930,627, filed on Aug. 16, 2001, now Pat. No. 6,737,083.

(51) Int. Cl.$^7$ .......................... A61K 38/47; A61K 7/00; A61K 7/48; A61K 33/14; A61K 33/00
(52) U.S. Cl. ................. 424/94.61; 424/94.6; 424/94.4; 424/70.1; 424/401; 424/600; 424/617; 424/663; 424/665; 424/667; 424/673; 424/677; 424/678; 424/679; 424/680; 424/681; 424/682; 424/722; 424/723; 514/829; 514/844; 514/849; 514/859; 514/863; 514/865; 514/886; 514/887; 514/928; 514/568
(58) Field of Search ............................... 424/70.1, 401, 424/600, 617, 663, 665, 667, 673, 677, 678, 424/679, 680, 681, 682, 722, 723, 94.61, 424/94.4, 94.6; 514/844, 886, 887, 829, 849, 514/859, 863, 865, 928, 568

(56) References Cited

U.S. PATENT DOCUMENTS

| | | |
|---|---|---|
| 4,141,825 A | 2/1979 | Conger |
| 4,160,727 A | 7/1979 | Harris, Jr. |
| 6,030,535 A | 2/2000 | Hayashi et al. |

FOREIGN PATENT DOCUMENTS

JP 2001-172186 * 6/2001

OTHER PUBLICATIONS

Chemical Abstracts 135:66222; abstracting JP 2001-172186 (Jun. 2001).*

* cited by examiner

*Primary Examiner*—John Pak
(74) *Attorney, Agent, or Firm*—Oltman, Flynn & Kubler

(57) ABSTRACT

A skin treatment mixture for treating pierced skin such as that resulting from a body piercing procedure includes sea salt, lysozyme and reconstituted ocean water. The reconstituted ocean water preferably is the product of reverse osmosis of water. The skin treatment mixture preferably additionally includes sodium benzoate to act as a preservative. A method of producing a skin treatment mixture includes the steps of providing a quantity of purified water; adding a quantity of sea salt to the quantity of purified water; boiling the purified water and sea salt; cooling the purified water and sea salt; adding a quantity of lysozyme to the purified water and sea salt; sterilizing the mixture and testing it for bacteria. A method of treating a pierced skin area includes the step of applying to the pierced area a reconstituted ocean water mixture of sea salt and lysozyme.

17 Claims, 1 Drawing Sheet

TOPICALLY APPLIED RECONSTITUTED OCEAN WATER MIXTURE AND METHOD OF PRODUCING AND USING THE MIXTURE

This application is a continuation-in-part of application Ser. No. 09/930,627 filed on Aug. 16, 2001, now U.S. Pat. No. 6,637,083 B2, dated May 18, 2004.

BACKGROUND OF THE INVENTION

1. Field of the Invention

The present invention relates generally to the field of topical skin treatments. More specifically the present invention relates to a reconstituted ocean water skin treatment mixture for topical application to the skin of a person for cleaning and healing and to methods of producing the mixture and of using the mixture to treat a pierced area of the skin of a person. The mixture includes purified ocean water, sea salt, and the natural enzyme lysozyme, mixed in critical ranges of percentage by weight and preferably additionally including the preservative sodium benzoate to enhance shelf life. The method of producing the mixture preferably includes the steps of boiling purified water and sea salt for ten minutes, adding sodium benzoate after a certain salinity level is reached, cooling the mixture, placing a quantity of lysozyme in a separate quantity of water to form a lysozyme solution, adding the lysozyme solution to the mixture, adding the sterilizing the water/mixture with ultraviolet radiation, and finally testing the resulting mixture for bacteria.

2. Description of the Prior Art

There have long been cleansing solutions such as hydrogen peroxide and antiseptics such as methylate for decontaminating and otherwise treating skin abrasions and lacerations, such as those produced during body piercing and for application to infected or inflamed inner throat membranes. Problems with these prior antiseptics have been that they often contain harsh and complex chemicals unfamiliar to consumers which can cause pain upon contact with wounds.

It is thus an object of the present invention to provide a skin treatment mixture having antibacterial, antiseptic, cleansing and healing properties which is suitable for removing dried discharge and lymph secretions safely while reducing bumps and scar tissue, reducing itching and increasing circulation to the treated area, and which is suitable for topical application to pierced skin areas such as those produced by body piercing or stitches closing a wound, to mouth sores and bed sores, to acne and to infected membranes of the throat, abscessed teeth, infected gums and canker sores, for tonsillitis, and also for skin tanning.

It is another object of the present invention to provide such a skin treatment mixture which is formed of components with which consumers are familiar and comfortable and which are safe, natural common, mild, pure and sterile, specifically including purified water.

It is still another object of the present invention to provide such a skin treatment mixture which is causes little or no stinging when applied to a wound.

It is finally an object of the present invention to provide such a skin treatment mixture which is inexpensive to manufacture.

SUMMARY OF THE INVENTION

The present invention accomplishes the above-stated objectives, as well as others, as may be determined by a fair reading and interpretation of the entire specification.

A skin treatment mixture is provided, including sea salt, lysozyme and purified water. The water is preferably ocean water. The skin treatment mixture preferably additionally includes sodium benzoate. A skin treatment mixture is provided, including sea salt, lysozyme and reconstituted ocean water. The reconstituted ocean water preferably is the product of reverse osmosis of water.

A skin treatment mixture is provided, including a quantity of purified water; sea salt to a salinity within the range of 0.800 grams per cubic centimeter to 1.030 grams per cubic centimeter; and lysozyme at a percentage by weight of dry lysozyme to purified water within the range of 0.001% to 1.00%. The skin treatment mixture preferably additionally includes sodium benzoate at a percentage by weight of sodium benzoate to purified water with a range of 0.001% to 1.6%. A skin treatment mixture is provided, including a quantity of purified water; sea salt to a salinity of 1.018 grams per cubic centimeter; and lysozyme at a percentage by weight of dry lysozyme to purified water of 0.02%. The skin treatment mixture preferably additionally includes sodium benzoate at a percentage by weight of 0.05%.

A method of producing a skin treatment mixture is provided, including the steps of providing a quantity of purified water; adding a quantity of sea salt to the quantity of purified water; boiling the purified water and sea salt; cooling the purified water and sea salt; and adding a quantity of lysozyme to the purified water and sea salt. The method preferably includes the additional steps of sterilizing the mixture and testing the mixture for bacteria. The method preferably includes the yet additional steps of placing a quantity of the lysozyme in a separate quantity of water to form a lysozyme solution; and adding the lysozyme solution to the mixture. Still further preferred method steps are boiling the purified water and salt solution for substantially ten minutes and adding a quantity of sodium benzoate after a purified water salinity level of 1.018 grams per cubic centimeter is reached. Finally, the mixture preferably is sterilized by exposure to ultraviolet radiation.

A method is yet further provided of producing a skin treatment mixture, including the steps of providing a quantity of purified water; adding sea salt to the quantity of purified water until a salinity within a range of 0.800 grams per cubic centimeter to 1.030 grams per cubic centimeter is reached; boiling the purified water and sea salt; cooling the purified water and sea salt; adding lysozyme to the purified water and sea salt to a percentage by weight of dry lysozyme to purified water within the range of 0.001% to 1.00%; and sterilizing the mixture. The mixture preferably is sterilized by exposure to ultraviolet radiation. A method is also provided of treating a pierced area of the skin of a person, including the steps of: applying to the pierced area a reconstituted ocean water mixture of sea salt and lysozyme.

BRIEF DESCRIPTION OF THE DRAWINGS

Various other objects, advantages, and features of the invention will become apparent to those skilled in the art from the following discussion taken in conjunction with the following drawings, in which.

DETAILED DESCRIPTION OF THE PREFERRED EMBODIMENTS

Figure 1:
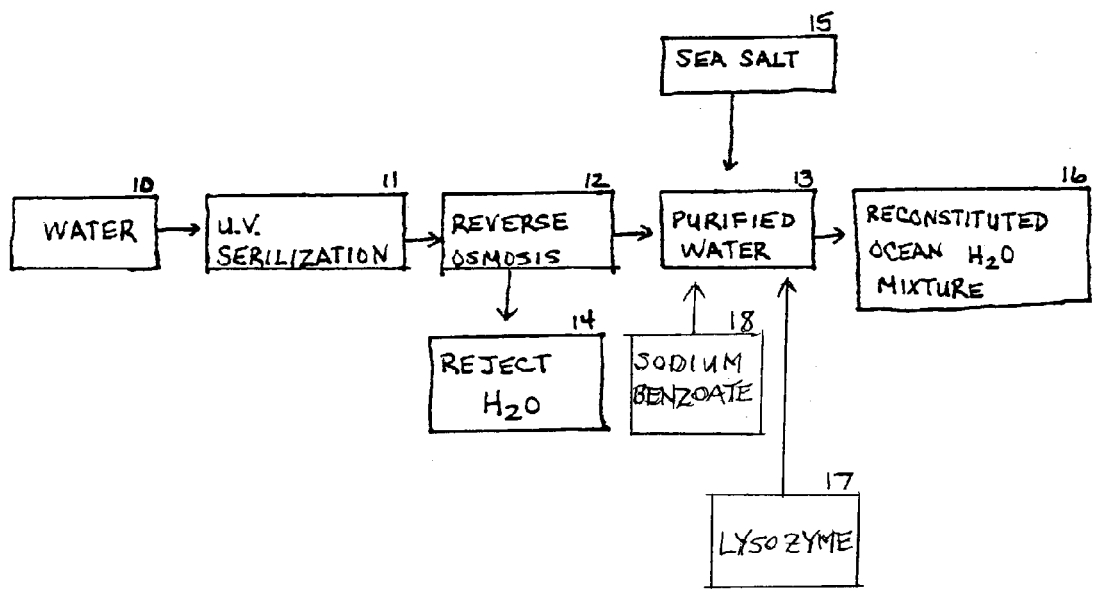
FIG. 1 is a flow chart of the novel process of making the present ocean water mixture.

As required, detailed embodiments of the present invention are disclosed herein; however, it is to be understood that the disclosed embodiments are merely exemplary of the invention which may be embodied in various forms. Therefore, specific structural and functional details disclosed herein are not to be interpreted as limiting, but merely as a basis for the claims and as a representative basis for teaching one skilled in the art to variously employ the present invention in virtually any appropriately detailed structure.

Reference is now made to the drawings, wherein like characteristics and features of the present invention shown in the various FIGURE are designated by the same reference numerals.

First Preferred Embodiment

Referring to FIG. 1, a skin treatment mixture 16 for topical application to a pierced area of a human body, such an area subjected to a body piercing procedure in a tattoo parlor, is disclosed. The components are combined as follows: sea salt 15 is added to a quantity of purified ocean water 13 until a salinity within the critical range of 0.800 grams per cubic centimeter to 1.030 grams per cubic centimeter is reached, and lysozyme 17 is added until a critical percentage by weight of dry lysozyme to purified water 13 of 0.001% to 1.00% is reached. The preferred specific proportions are: salinity from sea salt of 1.018 grams per cubic centimeter, and a percentage by weight of dry lysozyme 17 to purified ocean water of 0.02%. The mixture 16 preferably additionally includes the preservative sodium benzoate in a critical percentage range by weight of 0.001% to 1.6%, and a preferred specific percentage by weight of 0.05%, to enhance mixture 16 shelf life.

Method

In practicing the invention, the following method may be used. The preferred method steps for producing the mixture 16 include providing purified water 13, boiling the purified water 13 and sea salt 15 for ten minutes, adding sodium benzoate 18 after salinity level of 1.018 grams per cubic centimeter is reached, which is the same level found naturally in the human body and in clean ocean water, cooling the mixture, placing a quantity of lysozyme 17 in the porportion set forth above in a separate quantity of water to form a lysozyme solution, adding the lysozyme solution to the mixture, sterilizing the mixture with ultraviolet radiation, and finally testing the resulting mixture 16 for bacteria. The lysozyme is added to a separate quantity of water before being added to the mixture to prevent a possible unwanted chemical reaction.

The purified water 13 preferably is provided by subjecting water 10 to ultraviolet sterilization 11 and to reverse osmosis 12 to produce purified water 13 as well as reject water 14 which may be discarded or used for a purpose unrelated to the production of the present reconstituted ocean water mixture. Equipment of known design is used to perform this reverse osmosis. The purified water product 13 of the reverse osmosis operation is then mixed in the proportions set forth above with sea salt 15 and with lysozyme 17 to produce a liquid mixture 16 with a high salt concentration that may be applied topically to the pierced area of the user skin.

The Components

The sea salt 15 component of the present mixture 16 is a commercially available product used by many chefs as a condiment or seasoning to replace common table salt, and it has the purity required for human ingestion. The minerals and elements of sea salts are richer and more abundant than those of common table salt. Thus, the components of the present skin treatment mixture 16, the sea salt 15, the lysozyme 17 and the reverse osmosis purified water 13 are of very high purity to guard against infection or other harm to a wound or the surrounding skin area during the healing process that takes place after a body piercing operation.

The lysozyme 17 component is an enzyme which is harmless to and naturally produced by the human body. Lysozyme 17 is found in tears, sweat, saliva and urine and is capable of fighting infection by killing bacteria for periods of four to six hours. This enzyme also forms a shield around healthy cells to protect them from bacteria.

An optional additional component of the mixture 16 is sodium benzoate 18, which is a known preservative. Sodium benzoate 18 prevents airborne bacteria from invading the mixture 16 so that the mixture 16 remains sterile, and thus enhances mixture 16 shelf life.

The reconstituted ocean water mixture 16 produced as described with reference to FIG. 1 also may be used as a throat spray to cleanse and heal the infected membranes of the pharynx. The reconstituted ocean water mixture 16 can also be used to safely cleanse and heal a variety of other ailments including tonsillitis, abscessed teeth, infected gums and canker sores.

Although ocean water is the most abundant substance on the surface of the planet (approximately 78%), this invention represents the first attempt ever to reconstitute ocean water by purifying and sterilizing the water and then combining it with the natural enzyme lysozyme 17 and the inherent trace elements and minerals which are found in sea salt 15 for the commercial purposes described herein.

While the invention has been described, disclosed, illustrated and shown in various terms or certain embodiments or modifications which it has assumed in practice, the scope of the invention is not intended to be, nor should it be deemed to be, limited thereby and such other modifications or embodiments as may be suggested by the teachings herein are particularly reserved especially as they fall within the breadth and scope of the claims here appended.

I claim as my invention:

1. A skin treatment mixture comprising: sea salt, lysozyme and purified product of reverse osmosis of water.

2. The skin treatment mixture of claim 1, wherein said water is ocean water.

3. A skin treatment mixture comprising: sea salt lysozyme, purified water, and sodium benzoate.

4. A skin treatment mixture, comprising:
a quantity of purified water;
sea salt to a salinity within the range of 0.800 grams per cubic centimeter to 1.030 grams per cubic centimeter; and lysozyme at a percentage by weight of dry lysozyme to purified water within the range of 0.001% to 1.00%.

5. The skin treatment mixture of claim 4, additionally comprising sodium benzoate at a percentage by weight of sodium benzoate to purified water with a range of 0.001% to 1.6%.

6. A skin treatment mixture, comprising:
   a quantity of purified water;
   sea salt to a salinity of 1.018 grams per cubic centimeter;
   and lysozyme at a percentage by weight of dry lysozyme to purified water of 0.02%.

7. The skin treatment mixture of claim 6, additionally comprising sodium benzoate at a percentage by weight of sodium benzoate to purified water of 0.05%.

8. A method of producing a skin treatment mixture, comprising the steps of:
   providing a quantity of purified water;
   adding a quantity of sea salt to the quantity of purified water;
   boiling the purified water and sea salt;
   cooling the purified water and sea salt;
   and adding a quantity of lysozyme to the purified water and sea salt.

9. The method of claim 8, comprising the additional step of sterilizing the mixture.

10. The method of claim 8, comprising the additional step of testing the mixture for bacteria.

11. The method of claim 8, comprising the additional steps of:
   placing the quantity of lysozyme in a separate quantity of water to form a lysozyme solution;
   and adding the lysozyme solution to the mixture.

12. The method of claim 8, wherein the purified water and salt solution is boiled for substantially ten minutes.

13. The method of claim 8, comprising the additional step of:
   adding a quantity of sodium benzoate after a purified water salinity level of substantially 1.018 grams per cubic centimeter is reached.

14. The method of claim 9, wherein the mixture is sterilized by exposure to ultraviolet radiation.

15. A method of producing a skin treatment mixture, comprising the steps of:
   providing a quantity of purified water;
   adding sea salt to the quantity of purified water until a salinity within a range of 0.800 grams per cubic centimeter to 1.030 grams per cubic centimeter is reached;
   boiling the purified water and sea salt;
   cooling the purified water and sea salt;
   adding lysozyme to the purified water and sea salt to a percentage by weight of dry lysozyme to purified water within the range of 0.001% to 1.00%;
   and sterilizing the mixture.

16. The method of claim 15, wherein the mixture is sterilized by exposure to ultraviolet radiation.

17. A method of treating a pierced area of the skin of a person comprising the steps of: applying to the pierced area a mixture comprising the product of reverse osmosis of water, sea salt, and lysozyme.

* * * * *